United States Patent
Dong et al.

(10) Patent No.: US 10,517,705 B2
(45) Date of Patent: Dec. 31, 2019

(54) METHOD OF FORMING A UNIFORM COSMETIC OR THERAPEUTIC COATING ON TEETH

(71) Applicant: COLGATE-PALMOLIVE COMPANY, New York, NY (US)

(72) Inventors: Rong Dong, East Brunswick, NJ (US); Guofeng Xu, Plainsboro, NJ (US); Shaotang Yuan, East Brunswick, NJ (US); James Thomas, Highland Park, NJ (US); Kevern Fraser, East Orange, NJ (US)

(73) Assignee: Colgate-Palmolive Company, New York, NY (US)

( * ) Notice: Subject to any disclaimer, the term of this patent is extended or adjusted under 35 U.S.C. 154(b) by 5 days.

(21) Appl. No.: 15/344,450

(22) Filed: Nov. 4, 2016

(65) Prior Publication Data
US 2017/0128181 A1    May 11, 2017

Related U.S. Application Data

(60) Provisional application No. 62/251,289, filed on Nov. 5, 2015.

(51) Int. Cl.
*A61C 19/06* (2006.01)
*A61M 11/00* (2006.01)
*A61C 3/00* (2006.01)

(52) U.S. Cl.
CPC ............ *A61C 19/063* (2013.01); *A61C 3/005* (2013.01); *A61C 19/066* (2013.01); *A61M 11/006* (2014.02)

(58) Field of Classification Search
CPC ........ A61K 6/00; A61K 6/0023; A61K 6/083; A61Q 11/00; A61C 5/00
(Continued)

(56) References Cited

U.S. PATENT DOCUMENTS

| 5,776,435 A | 7/1998 | Gaffar et al. |
| 6,586,483 B2 * | 7/2003 | Kolb ............... C08J 9/0066 |
| | | 521/91 |

(Continued)

FOREIGN PATENT DOCUMENTS

| EP | 2399547 | 12/2011 |
| WO | WO 2013/093798 | 6/2013 |

OTHER PUBLICATIONS

Sherwood Pumps, 2001, "Classification Category Symbol Color Code Approximate VMD," jhttp://www.shemoodpumps.com/EileAttaehments/Spray/en-jus/Spray%20Ti%20Classification%20by%20Droplet%20Size.pdf.*
(Continued)

*Primary Examiner* — Wade Miles
*Assistant Examiner* — Matthew P Saunders (57) ABSTRACT

Disclosed is a method of forming a uniform coating onto a tooth surface, which method includes: forming droplets by spraying an orally acceptable coating material through a spray nozzle, and depositing the droplets onto the tooth surface to thereby form a uniform coating. In the method, the droplets have a volume-averaged droplet size of about 1 μm to about 100 μm, a spray including the droplets travels from a tip of the spray nozzle towards the tooth surface at a spray rate of less than about 10 milliliters/minute, and the droplets include a film-forming polymer, a therapeutic agent and/or a cosmetic agent.

12 Claims, 3 Drawing Sheets

Before Coating

After Coating (58) Field of Classification Search
USPC .................................................... 433/217.1
See application file for complete search history.

(56) References Cited

U.S. PATENT DOCUMENTS

| | | | | |
|---|---|---|---|---|
| 6,811,805 | B2* | 11/2004 | Gilliard | B29D 11/00317 |
| | | | | 427/164 |
| 2003/0168772 | A1* | 9/2003 | Palaniappan | A47G 21/183 |
| | | | | 264/209.1 |
| 2004/0162375 | A1 | 8/2004 | Mahfuza et al. | |
| 2005/0076831 | A1 | 4/2005 | Gilliard et al. | |
| 2008/0299520 | A1 | 12/2008 | Mahfuza et al. | |
| 2010/0021867 | A1* | 1/2010 | Altshuler | A61C 1/0046 |
| | | | | 433/215 |
| 2013/0052146 | A1 | 2/2013 | Jie et al. | |
| 2013/0079733 | A1* | 3/2013 | Burt | B05B 7/0012 |
| | | | | 604/290 |
| 2013/0277462 | A1 | 10/2013 | Baltz | |
| 2014/0339340 | A1 | 11/2014 | Duineveld et al. | |
| 2015/0017601 | A1 | 1/2015 | Fish et al. | |

OTHER PUBLICATIONS

Tarcha et al., "The Application of Ink-Jet Technology for the Coating . . . ", Annals of Bioengineering, 2007, 35:1791-1799.
International Search Report and Written Opinion of the International Searching Authority in International Application No. PCT/US2016/060715, dated Feb. 20, 2017.
Sherwood Pumps, 2001, "Classification Category Symbol Color Code Approximate VMD," http://www.sherwoodpumps.com/FileAttachments/Spray/en-us/Spray%20Tip%20Classification%20by%20Droplet%20Size.pdf.

* cited by examiner

PRIOR ART

METHOD OF FORMING A UNIFORM COSMETIC OR THERAPEUTIC COATING ON TEETH

CROSS-REFERENCE TO RELATED PATENT APPLICATIONS

This application claims the benefit of priority to U.S. Provisional Patent Application Ser. No. 62/251,289 filed Nov. 5, 2015, the entirety of which is incorporated herein by reference.

BACKGROUND

It is desirable to provide an even coating on tooth surfaces to deliver cosmetic and/or therapeutic agents in a uniform manner. Cosmetic and/or therapeutic agents may be readily applied by painting the agents onto tooth surfaces using a cosmetic brush or other delivery devices, such as an applicator pen. Cosmetic whitening pigments, for example, may often be used in those cases where bleaching-based technologies are less desirable. However, achieving a high-quality coating of uniform thickness on teeth by using applicators, such as brushes, to paint cosmetic and/or therapeutic agents on teeth is difficult due to the curved tooth surface. Accordingly, there remains a desire in the art to provide methods which may be used to uniformly coat cosmetic and/or therapeutic agents on teeth.

BRIEF SUMMARY

The present disclosure is directed to a method of forming a uniform coating onto a tooth surface, which method includes: forming droplets by spraying an orally acceptable coating material through a spray nozzle, wherein the droplets have a volume-averaged droplet size of about 1 μm to about 100 μm, and wherein a spray including the droplets travels from a tip of the spray nozzle towards the tooth surface at a spray rate of less than about 10 milliliter/minute, wherein the droplets include at least one substance selected from a film-forming polymer, therapeutic agent and/or a cosmetic agent; and depositing the droplets onto the tooth surface to thereby form the uniform coating.

Further areas of applicability of the present disclosure will become apparent from the detailed description provided hereinafter. It should be understood that the detailed description and specific examples, while indicating typical embodiments, are intended for purposes of illustration only and are not intended to limit the scope of the disclosure.

DETAILED DESCRIPTION

The following description of the embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Figure 1:
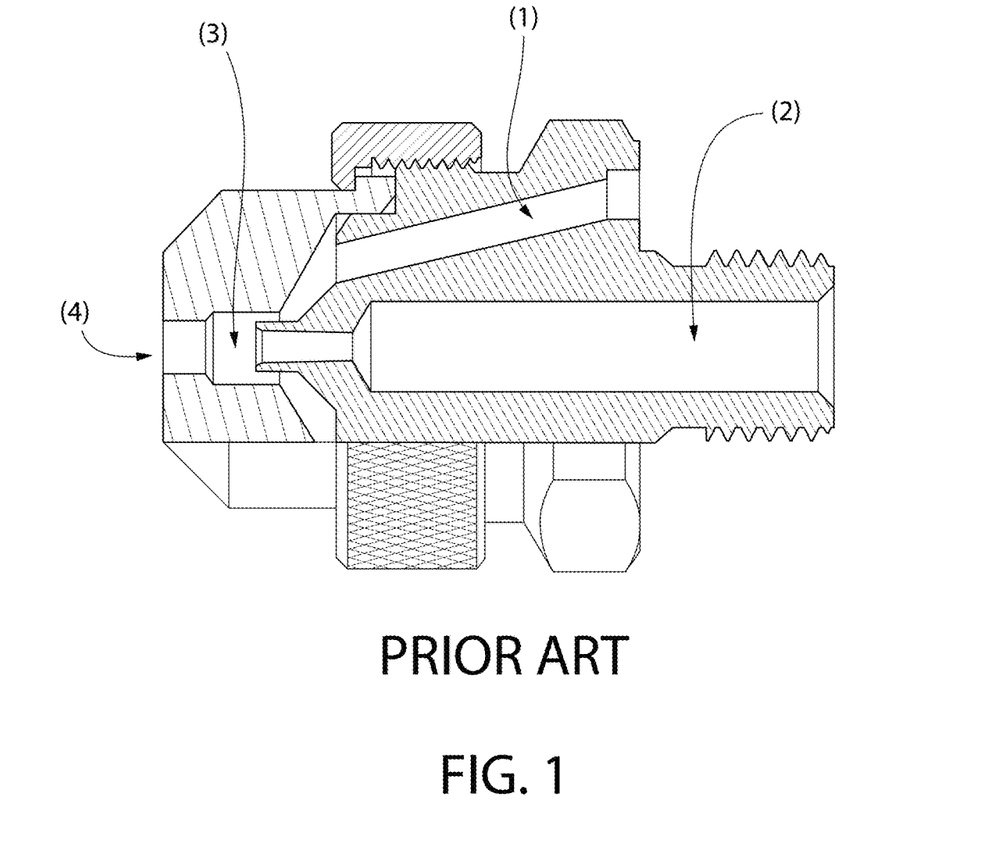
FIG. 1 shows a prior art internal-mix spray nozzle for gas pressure atomization.

The inventors have developed a method of forming a uniform coating, such as a film coating, on teeth using a spray coating process as described herein. Spray coating is employed in a wide range of industrial processes including paint application, air-condition humidification, and fuel injection. Spray coating has also been extensively used to coat tablets in the pharmaceutical industry. See, for example, Aliseda et al. "Atomization of liquids relevant to pharmaceutical tablet coating, Experiments and droplet size modeling," obtained from the world wide web on 22 Oct. 2015, maeresearch.ucsd.edu/lasheras/papers/pf.pdf, pages 1-17, page 2, paragraph 2. In regard to spray coating tablets, Pendey et al. (*AAPS Pharm Sci Tech.* 2014, 15: 296-305) teach that the process is quite complex, with multiple variables related to the substrate characteristics, coating formulation, processing equipment, and processing conditions. Id., at 296 and FIG. 1.

Unlike the pharmaceutical industry, which uses spray coating extensively, the present inventors are unaware of any literature regarding the use of spray coating to form uniform coatings on teeth in the oral cavity. Nevertheless, despite the apparent lack of guidance in the art and the extensive number of variable factors, which may affect coating formation on other substrates, the inventors were surprisingly able to provide a method of forming uniform coatings on teeth for the aesthetically pleasing and/or efficacious deposition of cosmetic and/or therapeutic agents.

Uniform Coating

The present disclosure is directed to forming a uniform coating on a substrate, e.g., a tooth surface. As used herein, a "tooth surface", means a tooth surface within an oral cavity. Typically, a "tooth surface" refers to the surface of a natural tooth; however, this phrase also encompasses dental implants or artificial teeth, which are made from synthetic materials, (e.g., titanium, ceramics, etc.), and which may be in the oral cavity or removed from the oral cavity before applying the instant coating.

The phrase "uniform coating" means that to the naked eye, the coating appears to be of a uniform thickness having a surface texture that appears smooth and free from defects, e.g., free from pinholes, dried droplets, streaks and particle agglomerates. In some embodiments, such as when the coating material is a whitening agent as described herein, the uniformity of the coating may be further indicated by the evenness of the tooth color.

As also described herein, the uniform coating may be achieved by delivering an orally acceptable coating material to a tooth surface 1) in the form of droplets having a volume-averaged droplet size ranging from about 1 μm to about 100 μm and 2) at a spray rate of less than about 10 milliliters per minute, such as less than 0.6 milliliters per minute. In some embodiments, as also described herein, the droplets are delivered at a distance of about 20 centimeters or less from the tooth surface since, e.g., greater distances may preclude the precise spraying of the coating material onto teeth in the oral cavity.

By depositing an orally acceptable coating material in the form of droplets onto the teeth according to the present method, a uniform coating may be achieved that has a surface texture comprising a surface roughness value and/or a surface waviness value that is substantially less than a surface roughness value and/or a surface waviness value of a coating that is not delivered to the teeth according to the recited ranges.

As used herein, "surface roughness" and/or "surface waviness" are components of surface texture. As is well known in the art, surface texture can be measured using surface profilometry, surface scanning methods or atomic force microscopy, for example. As used herein "surface roughness" is the high-frequency, short-wavelength component of a measured surface. Surface roughness may be quantified by the deviations in the direction of the normal vector of a real surface from its ideal form. If these deviations are large, the surface is rough; if they are small, the surface is smooth. As is well known to the ordinary artisan, surface roughness can be measured in terms of a number of parameters well known in the art, including, but not limited to, average surface roughness, Ra, maximum roughness depths on the sample surface, Rt, average maximum peak to valley heights, Rz, maximum surface roughness, R max and the arithmetic average height of roughness component irregularities from the mean line measured within the sampling length, Ra. Surface roughness can also be measured in terms of the average of the measured height deviations taken within the evaluation length or area and measured from the mean linear surface, i.e., Rq (also called RMS; root mean square roughness).

The term "waviness" describes the more widely spaced component of a surface texture. There are several parameters for expressing waviness, including average waviness, Wa, total waviness, Wt, Waviness spacing, Wsm and root mean square waviness, Wq.

The phrase "substantially less" in reference to a surface roughness value and/or a surface waviness value means that one or more of these values is at least about 15% less, such as at least about 25% less, such as at least about 40% less, such as at least about 50% less, such as at least about 100% less or such as least 200% less than a surface roughness value and/or a surface waviness value obtained from a control coating.

As used herein, a "control coating" means that a coating was formed on a tooth surface in the same manner as the instant method, except that the droplet size and/or the spray rate as defined below is outside of the ranges specified in 1) and 2) above.

Droplets

In some embodiments, the present method includes forming droplets by spraying an orally acceptable coating material through a spray nozzle. As used herein, "spraying" refers to a process that causes atomization of a fluid, i.e., the break-up of a fluid into droplets.

The spraying process of the present disclosure may comprise any art-known atomization process. For example, in some embodiments, the instant spraying process includes fluid pressure atomization. In this embodiment, fluid pressure is converted to momentum as a fluid is sprayed through a spray nozzle. More particularly, in fluid pressure atomization (or "airless atomization") high pressure forces fluid, such as the instant orally acceptable coating material, through a small nozzle. The fluid emerges as a solid stream or sheet at high speed. The friction between the fluid and the air disrupts the stream, breaking it into fragments initially and ultimately, into droplets. Spray nozzles suitable for fluid pressure atomization are known in the art and are commercially available from, for example, Spray Sizer Company, Markham, Ontario, Canada.

In another embodiment, the instant spraying process includes centrifugal force (rotary) atomization. In this embodiment, fluid from a spray nozzle is introduced at the center of a spinning cup or disk. Centrifugal force carries the fluid to the edge of the disk and throws the fluid off the edge. The liquid, such as the orally acceptable coating material of the present disclosure, forms ligaments or sheets that break into fine droplets. With the same rotational speed, at low flow rates of fluid, droplets form closer to the edge of the disk than with higher flow rates. The spray pattern tends to move radially away from the disk or cup in all directions. Typically, the flow rate and disk speed are independently controlled. Further, an electrostatic charge is typically applied to the spray to attract the droplets to a target object, e.g., a tooth surface of the present disclosure. Rotary nozzles for use with the present method are known in the art and are commercially available from, for example, Nordson Corporation, Westlake, Ohio.

In another embodiment, the instant spraying process uses an electric charge received by a fluid (such as the present orally acceptable coating material) as an energy source for electrostatic atomization. Electrostatic atomization exposes a fluid to an intense electric field between the charged atomizer and a substrate, such as a tooth surface. The charge transfers to the fluid and repulsive forces between the atomizer and the fluid tear droplets from the atomizer and send them toward the substrate. Electrostatic spray nozzles for use with the present method are known in the art and are commercially available from, for example, Elliot Equipment Corporation, Indianapolis.

In another embodiment, the instant spraying process uses ultrasonic atomization. In this embodiment, atomization is achieved using an electromechanical device that vibrates at a very high frequency, e.g. 20 Hz to 200 kHz. Fluid passes over the vibrating surface and the vibration at ultrasonic frequencies causes the fluid to break into droplets. The ultrasonic vibration energy is typically produced by piezoelectric transducers. Piezoelectric transducers are well known in the art and comprise a piezoelectric material, i.e. a material that converts mechanical energy into electrical energy and vice versa. Ultrasonic atomization may result in droplets having the range of sizes described herein, even when higher viscosity fluids are used. Accordingly, in some embodiments, ultrasonic atomization may be used with the coating materials described herein, wherein a viscosity of the coating material ranges from about 1 mPa·S to about 100 mPa·S. Ultrasonic spray nozzles for use with the present method are known in the art and are commercially available from, for example, Sonaer Inc., Framingdale, N.Y.

In other embodiments the spraying process atomizes droplets using ink jet related printing technologies. For example, voltages may be applied to a glass capillary chamber filled with a fluid, e.g., an orally acceptable coating material of the present disclosure. By applying voltages to a wall of the glass capillary with a piezoelectric crystal bonded to the glass capillary, a distortion is caused that bows the walls outwards. This distortion causes the pressure of the fluid to drop, drawing more fluid into the capillary. When the voltage is released and the walls return to their original positions, a droplet is expelled through a print spray nozzle orifice.

Other methods for atomization include the use of thermal jet printing processes where an electric current is used to create a high temperature, which vaporizes a portion of a liquid in a chamber, which then generates a pressure that in turn fires a droplet through a spray nozzle orifice. Such ink jet related printing technologies for atomization are known in the art and are described, for example, in Tarcha et al., *Annals of Biomedical Engineering*, 2007, 35(10):1791-9 and U.S. Patent Publication No. 2005/0076831, which are each herein incorporated by reference in its entirety.

More typically, the instant spraying process uses gas pressure atomization. In some embodiments, the gas used for gas pressure atomization is nitrogen, oxygen, helium, carbon dioxide, sulfur hexafluoride, chlorofluorocarbons, methane, fluorocarbons, nitrous oxide, xenon, propane, n-pentane or the like. Typically, however, the gas is air. Atomization results from the relative difference in velocity between a fluid, e.g., the orally acceptable coating material of the present disclosure and a gas. In some embodiments, the orally acceptable coating material enters a spray nozzle at a lower speed than the gas speed, resulting in friction between the liquid and gas, thus accelerating and disrupting the fluid stream, causing atomization.

In some embodiments, an internal-mix spray nozzle is used for gas pressure atomization. An exemplary internal-mix nozzle is shown in FIG. 1. In this embodiment, the atomization gas and fluid travel through feeds (1) and (2) respectively. Fluid and air are then mixed in the annular area (3) resulting in atomization of the fluid before being forced through a nozzle tip (4). As the mixture of air and fluid passes through the nozzle tip (4), its pressure is significantly reduced.

In some embodiments, atomization is achieved using air pressure atomization with a device, such as an airbrush. A typical airbrush operates by passing a stream of compressed gas (e.g. air) through a spray nozzle, which generates a localized zone of reduced pressure or suction. This suction is used to draw a liquid, e.g., an orally acceptable coating material of the present disclosure, from a connected reservoir. The velocity of the compressed gas stream atomizes the liquid into droplets as it is driven past a metering device where it is thereafter directed to a substrate, e.g., a tooth. The amount of delivered liquid is typically controlled via a trigger that controls the compressed gas flow. Suitable airbrushes include those commercially available from TCP Global Corporation, San Diego, Calif., such as Master Airbrush® Brand Model VC16-B22.

The above-described atomization processes result in a "spray", i.e., an aggregate of all droplets formed. Typically, the spray contains a range of statistically distributed droplet sizes. The size of the droplets may be determined using techniques well-known to an ordinary artisan, e.g., imaging (microscopy and the use of high speed video cameras) and laser light scattering techniques. For example, instruments are commercially available, which instantly sample a large number of droplets in a given volume, e.g., from Malvern Instruments Company Worcestershire, United Kingdom.

In various embodiments, the spray comprises droplets having a volume-averaged droplet size ($D_v$) ranging from about 1 micrometer (μm) to about 100 μm, such as from about 5 μm to about 50 μm, more typically from about 5 μm to about 30 μm. $D_v$ may be calculated using the following formula:

$$D_v = \sum_i (N_i D_i^4) \Big/ \sum_i (N_i D_i^3)$$

with $N_i$ being the total number of droplets with diameter $D_i$.

In various embodiments, the distribution of the droplet size is narrow. For example, in some embodiments, less than about 10% of the droplets delivered to the tooth surface have a diameter greater than about 100 μm or less, such as less than about 5%, such as less than about 0.1%. In some embodiments, this narrow droplet size distribution results in a uniform coating without visible defects. For example, since the human eye can only discern particles having a diameter greater than about 116 μm, omitting droplet sizes having a diameter of more than about 100 μm from delivery to the tooth surface is likely to preclude the visibility of dried droplets on the teeth, which may detract from an aesthetically pleasing coating.

In some embodiments, the gas flow rate, such as a gas flow rate used during gas pressure atomization, such as an air flow rate, affects the size of the droplets. For example, higher flow rates are associated with the production of smaller droplets, while lower flow rates, such as a gas flow rate below 4 cubic feet per hour, may preclude atomization of the coating material, even when the coating material has a low viscosity. Accordingly, in some embodiments, the foregoing droplet size is achieved by maintaining a flow rate of a gas, such as air, during atomization, which is in the range of about 4 cubic feet per hour to about 30 cubic feet per hour, such as about 6 cubic feet per hour to about 20 cubic feet per hour. Outside of the upper end of these ranges, the effect of gas flow rate on droplet size is typically minimal.

In some embodiments, the viscosity of the coating material also affects droplet size. Accordingly, in order to achieve droplets having a volume-averaged size ranging from about 1 μm to about 100 μm as described herein, the viscosity of the orally acceptable coating material, in some embodiments, ranges from about 1.1 mPa·S to about 100 mPa·S, more typically about 1.1 mPa·S to about 25 mPa·S and even more typically about 3 mPa·S to about 15 mPa·S. When gas pressure atomization, such as air pressure atomization is used with the instant method, the viscosity of the coating material is typically less than about 15 mPa·S to avoid blockage of the spray nozzle.

Spray Rate

In some embodiments, the spray, as described herein, travels towards the substrate (the tooth surface) at a rate of less than about 10 millimeters per minute after exiting the nozzle tip (referred to herein as the "spray rate"). In other embodiments, the spray rate is less than about 1 millimeter per minute. In some embodiments, the spray rate is less than about 0.6 milliliters per minute. Typically, slower spray rates, such as those less than about 0.6 milliliters per minute, allow for a more precise control of the spray.

In some embodiments, an orifice diameter of a spray nozzle, which is used during atomization, such as air pressure atomization, may impact the spray rate. For example, a large orifice diameter will result in a faster spray rate in comparison to the spray rate achieved using a spray nozzle with a smaller orifice diameter, even if the air flow rate and the viscosity of the coating material remain constant. Typically, a spray nozzle having an orifice diameter ranging from about 0.5 millimeters (mm) or less, such as about 0.3 mm or less, such as about 0.2 mm is used during atomization of the coating material, such as during air pressure atomization of the coating material. Typically, a spray nozzle having an orifice diameter of about 0.2 mm is used with the present uniform coating method.

In some embodiments, uniformity of the coating is achieved on the present substrates by combining particular spray rate ranges with particular spray distances. As used herein, a "spray distance" refers to the distance between a spray nozzle tip and a substrate, e.g., a tooth surface within the mouth. Typically, faster spray rates are used with greater spray distances to avoid visible coating defects, such as over-wetting. However, in various embodiments, the visible defects associated with spray rates greater than about 10 milliliters per minute, such as over-wetting, coarseness, uneven color and pinholes, are typically not mitigated by a spray distance, even as great as 20 cm. Spray distances greater than 20 cm also may not be practical, as noted above, since they do not allow for precise spraying of the droplets onto a tooth surface. Accordingly, in various embodiments, the spray rate does not exceed about 10 milliliters per minute.

In typical embodiments, when a spray rate, which is less than about 10 milliliters per minute, is used during atomization, such as air atomization, the spray distance ranges from about 1 cm to about 20 cm. In other typical embodiments, when a spray rate of less than about 10 milliliters per minute, such as less than about 8 milliliters per minute, such as less than about 5 milliliters per minute, such as less than about 2 milliliters per minute, is used during atomization, such as air atomization, the spray distance is about 20 centimeters (cm). In other embodiments, when a spray rate from about 1 milliliter per minute to about 0.6 milliliters per minute is used during atomization, such as air atomization, the spray distance is typically about 5 cm to about 10 cm. In yet still other embodiments, when a spray rate less than about 0.6 milliliters per minute is used during atomization, such as air atomization, the spray distance is about 5 cm or less. Typically, larger spray distances, e.g. about 12 cm to about 20 cm, are used with the present method, particularly with spray rates greater than about 2 milliliters per minute since larger spray distances may result in a more aesthetically pleasing coating, e.g. a drier-appearing coating finish throughout the tooth surface.

In some embodiments, the viscosity of the coating material also affects the spray rate. Accordingly, in some embodiments, a spray rate of less than about 10 milliliters per minute as described herein may be achieved by atomizing an orally acceptable coating material having a viscosity ranging from about 1.1 mPa·S to about 100 mPa·S, more typically about 1.1 mPa·S to about 25 mPa·S and even more typically about 3 mPa·S to about 15 mPa·S. As noted above, when gas pressure atomization, such as air pressure atomization is used with the claimed method, the viscosity of the coating material is typically less than 15 mPa·S to avoid blockage of the nozzle.

In some embodiments, the gas flow rate, such as the gas flow rate used during gas pressure atomization, such as air pressure atomization, affects the spray rate. Accordingly, in some embodiments, the foregoing spray rates are achieved by maintaining a flow rate of the gas, such as air, in the range of about 4 cubic feet per hour to about 30 cubic feet per hour, such as about 6 cubic feet per hour to about 20 cubic feet per hour.

Orally Acceptable Coating Material

The droplets of the present method are formed from an orally acceptable coating material. As used herein, "orally acceptable" means that the coating material and the components thereof are safe for use in the mouth at the levels required.

Vehicle

In some embodiments, the coating material is a composition comprising an orally acceptable vehicle. The orally acceptable vehicle may include an orally acceptable solvent, such as ethanol, methanol, isopropanol, butanol, water, methylene glycol, ethylene glycol, propylene glycol, butylene glycol, neopentyl glycol, hexylene glycol, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, and glycerin. Typically, the orally acceptable solvent is a volatile solvent such as ethanol.

The orally acceptable solvent may be present in an amount of about 0.1% to about 99.5% by weight based upon the total weight of the mixture, although about 60% to about 95% by weight based upon the weight of the total mixture is typical, with an amount of 80%-90% by weight being further typical.

In some embodiments, the orally acceptable vehicle comprises a film-forming polymer instead of, or in addition to, the orally acceptable solvent. As used herein, a "film forming polymer" is understood to encompass polymers, prepolymers and/or monomers capable of forming alone, or in the presence of at least one additional agent, a continuous and adherent film on a tooth substrate. The term "prepolymer" refers to a system of monomers that have been reacted to an intermediate molecular mass state. This material is capable of further polymerization by reactive groups to reach a fully cured high molecular weight state. As such, mixtures of reactive polymers with un-reacted monomers may also be referred to as prepolymers. A "monomer" is a molecule that may bind chemically to other molecules to form a polymer.

Film-forming polymers may be any of the natural polymers including commonly used gums, resins, exudates, animal rendering products and byproducts, such as gelatin and keratin, plant extracts, alginates, cellulose, galactomannans, bacterial products, such as Xanthan gum, and derivatives of these natural polymers, including methyl-, hydroxypropyl-, acetate phthalate, acetate, methoxy, hydroxypropoxy, acetyl, phthalyl, hydrolysates, and salts (Li, Na, K, Ca, Mg, Al, Zn, B, Fe, Cu, Ni), or combinations thereof or associated reaction byproducts. They may also be synthetic polymers, including homopolymers, copolymers, interpolymers, block polymers, or graft polymers, either crosslinked or substantially linear, derived from monomers known in the film-forming arts such as (meth)acrylic acid homo- and copolymers, including those which are directed mainly at olefinically unsaturated moieties of various functionality and substitution. Examples of suitable-film forming polymers include, but are not limited to, polyurethanes, acrylic polymers, vinyl polymers, silicone polymers, and derivatives thereof. Particularly suitable film forming polymers include acrylate/octylacrylamide copolymers, for example 2-propenoic acid, 2-methyl-,2-methylpropyl ester, polymer with 2-propenoic acid and N-(1,1,3,3-tetramethylbutyl)-2-propenamide, (e.g., DERMACRYL® 79).

In some embodiments, the film protects against staining and bacteria. In other embodiments, the film contains a whitening agent and/or a therapeutic agent as described herein.

In some embodiments, the film-forming polymer comprises for example, a bisphenol derivative for use as a dental sealant. Such bisphenol A derivatives include bis-GMA, bis-DMA, bisphenol-A ethoxylate dimethacrylate (bis-EMA) and urethane-modified bis-GMA. In these embodiments, the droplets as described herein may be coated onto a chewing surface of the teeth, e.g., the premolars and molars. The film, which is formed after polymerization, that is after curing using visible light, for example, acts as a dental sealant. As used herein, a "dental sealant" is a film, which is used to prevent tooth decay. The sealant bonds into the depressions and grooves of the teeth by forming a protective shield over the enamel of each coated tooth.

In some embodiments, the film-forming polymer is present at an amount from about 0% to about 80% by weight of the present coating material, such as about 40% to about 80% by weight, such as about 60% to about 80% by weight. In other embodiments, the film-forming polymer may be present in the instant coating material in an amount ranging from about 15% to about 25% by weight, such as about 5% to about 20% by weight, such as about 13.5% or about 9% by weight.

Rheology modifiers, dispersants and/or plasticizers, which are well known to an ordinary artisan, may also be included in the present orally acceptable vehicle. The orally acceptable vehicle may be present in the coating material in an amount ranging from about 0.1% to about 99% by weight of the coating material, such as from about 25 to 85%, such as from about 45% to about 80% by weight of the present coating material.

Cosmetic and Therapeutic Agents

In some embodiments, the present orally acceptable coating material includes a cosmetic agent, such as a whitening agent. As used herein, a "whitening agent" is a material which effects whitening of a tooth surface to which it is applied. Any whitening agent known or developed in the art may be used in the present coating materials For example, in some embodiments, the present compositions include a whitening pigment. In some embodiments, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles and combinations thereof. The whitening pigment, such as titanium dioxide particles, may be in an amount that is sufficient to whiten the teeth.

In some embodiments, the whitening agent is a peroxide compound, such as hydrogen peroxide, calcium peroxide, peracids etc.

In various embodiments, the whitening agent comprises from about 4.1% to about 50% w/w, such as about 4.1% to about 40% w/w, such as about 4.1% to about 30% w/w of the present coating material, such as about 1% to 3%, such as about 1%. In other embodiments, the whitening agent, is present in a low concentration, e.g. about 0.01% to about 4%, such as about 0.1% to about 4%, such as about 0.01% to about 3%, such as about 0.05% to about 3%, such as about 0.075% to about 1%, such as about 0.1% to about 1.5%, such as about 0.01% to about 0.3%, such as about 0.1% to about 0.3% or about 0.1%.

In some embodiments, the active ingredient is a therapeutic agent. Suitable therapeutic agents include a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, the amount of fluoride in the present coating material ranges from about 0.1% to 1.1%, typically about 1.1%.

The therapeutic agent also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The therapeutic agent may also include an antimicrobial (e.g., antibacterial) agent, such as triclosan. An illustrative list of useful antibacterial agents is provided in U.S. Pat. No. 5,776,435 to Gaffar et al., the contents of which are incorporated herein by reference. One or more antimicrobial agents may be present in an antimicrobial effective total amount, typically about 0.05% to about 10%, for example about 0.1% to about 3%.

Other therapeutic agents include without limitation calcium ion sources, e.g. calcium carbonate, a zinc ion source, e.g., zinc citrate, a potassium ion source, e.g., potassium chloride or combinations thereof. If present, the amount of ion source in the present composition ranges from about 0.1% to 5%, typically about 1% by weight. A basic amino acid, e.g., arginine in free or salt form, may also be used as a therapeutic agent.

Deposition and Coating Formation

Once the droplets, which include film-forming polymers, cosmetic and/or therapeutic agents, are deposited onto the tooth surface using the spraying processes described herein above, a uniform coating is formed on the tooth by well known mechanisms, such as evaporation, coalescence, oxidation curing or by the use of curing agents such as UV light, visible light or heat. The particular mechanism, which is used to form the coating, will depend upon the particular coating materials used.

A coating formed by "evaporation", means that a carrier, such as an orally acceptably vehicle as described herein, e.g. ethanol, evaporates, leaving behind a solid coating without any chemical or structural change to the rest of the materials in the droplet, e.g., without any change to the film-forming polymer, the cosmetic agent and/or the therapeutic agent.

A coating, which is formed by coalescence means that, as a solvent evaporates from the droplets on the teeth, chains of film-forming polymers present in the droplets start to become more closely packed together. After enough solvent evaporates, the polymer chains become so tightly packed that they begin to fuse together, or coalesce, to form a coating.

In some embodiments, the coating is formed by oxidation curing. As is known in the art, oxidation curing is a two-step process for coating formation. First, the droplets dry by solvent evaporation, which exposes the film-forming polymer to air. Then the polymers react with oxygen from the air to further harden.

In some embodiments, the coatings are formed using a curing agent. In these embodiments, the coating material may include prepolymers and/or monomers. A curing agent, such as UV light, visible light or heat may be directed to the tooth surface after deposition of the droplets to facilitate a reaction between the prepolymers and/or monomers resulting in a film comprising high molecular weight polymers.

The time for the coating to form may vary from about 1 second to about 3 hours, such as from about 1 minute to about 30 minutes, such as from about 1 minute to about three minutes. In some embodiments, the coating may form in the above-described ranges, but may take longer to harden dependent upon the components of the coating material.

Faster spray rates, for example, spray rates of less than about 10 milliliters per minute to about 8 milliliters per minute. are generally associated with a longer drying time Accordingly, a drying time for a faster spray rate may, in a most typical embodiment, form and harden in less than about 3 minutes, whereas a slower spray rate, e.g. about 0.6 milliliters pre minute, may form and harden in less than about 1 minute.

In some embodiments, the formed coating ranges in thickness from about 0.1 μm to about 1500 μm, such as from about 1 μm to about 500 μm. Typically, the thickness of the uniform coating formed from the deposition of the droplets ranges from about 1 μm to about 100 μm.

EXAMPLES

Example 1. Spray Rate and Droplet Size Impact on Uniformity of Coatings

A. Formula Preparation

A liquid coating material was prepared for atomization. The coating material included the following ingredients: Anhydrous Ethyl Alcohol, 200 Proof, PHARMCO-AAPER Company, Brookfield, Conn.; Acrylates/Octylacrylamide Copolymer, DERMACRYL® 79, AkzoNobel Company, Surface Chemistry, Amsterdam, Netherlands; Hydrogenated Rosin, FORAL™ AX-E Fully Hydrogenated Rosin, Eastman Chemical Company, Kingsport, Tenn. and titanium dioxide ($TiO_2$), KRONOS Worldwide Inc., Chelmsford, Mass.

The liquid coating material was prepared by adding DERMACRYL® 79, Hydrogenated Rosin, $TiO_2$ and Ethanol to a spin mix jar. The mixture was then spin mixed at 3540 rpm for 4 minutes. A typical formula example is shown in Table 1, which has a viscosity of 10.5 mPa·S. By varying the polymer and rosin concentration, formulas with a range of viscosity were prepared.

TABLE 1

| Component | % | Weight (g) |
|---|---|---|
| DERMACRYL ® 79 | 9.0% | 0.9 |
| Hydrogenated Rosin | 4.5% | 0.45 |
| $TiO_2$ | 1.0% | 0.1 |
| EtOH | 85.5% | 8.55 |
| total | 100.0% | 10 |

B. Spray Parameters

The impact of two spray process parameters on uniform coating, droplet size and spray rate, was assessed under different conditions (Group A-E) as depicted in Tables 2-4, below. The coating material, which was used in these examples, was prepared as described above.

The droplet sizes were varied during atomization by adjusting the formula viscosity, air flow rate and/or the nozzle size of the airbrush. Air flow was controlled using an OMEGA F-2034 flow meter, Omega Engineering, Inc., Stamford, Conn. Volume-averaged droplet size was assessed using Spraytec, Malvern Instruments.

Transparent plastic substrates (60×15 mm Petri dishes) were coated with varied droplet sizes after atomization of the coating material with an airbrush (Master Airbrush® Brand Model VC16-B22 Airbrushing System and a MAS KIT-VC16 Black Portable Mini Airbrush Air Compressor).

Spray rates greater than 3 milliliters per minute were assessed by quantifying the total amount of time for 1 milliliter of coating material solution to spray out of the airbrush. Spray rates less than 3 milliliters per minute were assessed by capturing the spray in Petri dishes for 5 seconds, followed by weighing. Spray rate was then determined from the dry weight gain of the Petri dishes.

The transparent plastic substrates were visually assessed after coating for over-wetting, dripping, pinholes, coarseness, dried droplets, uniformity of thickness and evenness of color. In addition, the surface texture, including surface roughness and surface waviness, was characterized using a profilometer (MicroXAM 800 (KLA-Tencor Company, Milpitas, Calif.). Measurements were obtained using a 5× objective. Surface texture was assessed using the MicroXAM 800 software.

i. Impact of Spray Rate

For Group A, atomized coating material having a volume-averaged droplet size of less than 100 μm was sprayed onto a first group of Petri dishes using a spray rate of less than 0.6 milliliters per minute. A second group of Petri dishes was also sprayed with an atomized coating material having a volume-averaged droplet size of less than 100 μm using a spray rate greater than 0.6 milliliters per minute (Group B). The spray distance remained constant (about 5 centimeters) between Group A and B.

The results of the visual examination and surface texture assessment are shown in Table 2, below. Visual examination revealed that increasing the spray rate to more than 0.6 milliliters per minute, while using droplets having a volume-averaged droplet size of less than 100 μm, impacts coating uniformity. As described in Table 2, the Group B coating exhibited visible defects due to over-wetting in comparison to the uniform Group A coating. Moreover, the waviness and roughness values of the Group B coating were 2.4 and 1.7 times greater, respectively, than those of the Group A coating, further supporting the impact of spray rate on uniform coatings.

TABLE 2

Impact of spray rate on uniform coatings

| Group | Formula viscosity (mPa · S) | Air flow rate (cfh) | Nozzle | Droplet Size | Spray Rate | Spray Distance | Visual Examination | Sq P (nm) | Wq (nm) | Rq (nm) |
|---|---|---|---|---|---|---|---|---|---|---|
| A | 6-16 | 8-12 | 0.2 mm, <0.5 mm needle retraction | <100 μm | <0.6 ml/min, | ~5 cm | Uniform white coating. No visible defects | 799.2 ± 227.8 | 216.7 ± 51.7 | 671.9 ± 167.5 |

TABLE 2-continued

Impact of spray rate on uniform coatings

| Group | Formula viscosity (mPa · S) | Air flow rate (cfh) | Nozzle | Droplet Size | Spray Rate | Spray Distance | Visual Examination | Sq P (nm) | Wq (nm) | Rq (nm) |
|---|---|---|---|---|---|---|---|---|---|---|
| B | 6-16 | 8-12 | 0.2 mm, >0.5 mm needle retraction | <100 μm | >0.6 ml/min, | ~5 cm | Uneven coating with visible defects due to over-wetting | 1425.2 ± 542.9 | 522.9 ± 182.6 | 1127.7 ± 643.1 | ii. Impact of Droplet Size

In order to assess the significance of droplet size on coating uniformity, atomized coating material having a droplet size different from that of Group A as described above, was sprayed onto a third group of Petri dishes (Group C) at the same spray rate and spray distance as that of Group A, i.e., less than 6 milliliters per minute at a spray distance of about 5 cm. The atomized coating material for Group C contained a broader distribution of droplet sizes in comparison to the droplet size distribution used to form the uniform coating in Group A. In particular, 10% of the droplets used to coat the Group C Petri dishes had a droplet size of greater than 100 μm in diameter while the remaining 90% of the droplets had a droplet size of less than 100 μm in diameter. In contrast, almost all of the droplets in Group A had a droplet size of less than 100 μm in diameter.

Table 3 shows the results of the visual examination and the surface texture of the Group C coating. As is evident from Table 3, increasing the droplet size diameter to greater than 100 μm for 10% of the droplets significantly impacted coating uniformity in comparison to the Group A uniform coating, which is reproduced in Table 3 for comparison. As noted in Table 3, visual examination of the Group C coating revealed that a broader distribution of droplet size results in a course coating with visibly dried droplets. Moreover, the waviness and roughness values of the Group C coating were increased in comparison to those of Group A. In particular, the waviness and roughness values of the Sample C coating were 1.7 and 1.1 times greater, respectively, than those of Group A, demonstrating the negative impact of droplet sizes greater than 100 μm on uniform coating preparation.

adjusting spray distance, faster spray rates, i.e., spray rates of about 9.0 milliliters per minute (Group D) and about 10.3 milliliters per minute (Group E) were assessed in combination with an increase in spray distance. To achieve such a high spray rate, two airbrushes were used to spray the same surface simultaneously. Since it may be impractical for a consumer or a dental practitioner to precisely spray droplets onto teeth in the mouth at a spray distance of greater than 20 centimeters, this maximum practical distance was used to assess its impact on coating uniformity in combination with the faster spray rates.

As shown in Table 4, below, a uniform coating without visible defects may be obtained by delivering droplets having a volume-averaged droplet size of less than 100 μm at a high spray rate of 9.0 milliliters per minute, provided that the spray distance is increased to about 20 centimeters (Group D). In contrast, increasing the spray rate to a little over 10 milliliters per minute results in an uneven coating with visible defects due to wetting, even when the spray distance is 20 centimeters, the apparent maximum practical distance for spraying teeth (Group E).

Moreover, the waviness value of the Group E coating was twice as large as the waviness value of the uniform Group D coating. Furthermore, the difference in the roughness value of the Group E and Group D coating was even greater than the waviness value. In particular, the roughness value of the Group E coating was seven times as large as the roughness value for the Group D coating. Accordingly, the Table 4 data show that a uniform coating may be obtained when a spray rate faster than 0.6 milliliters per minute is used, but only if the spray distance is increased. Spray rates

TABLE 3

Impact of droplet size on uniform coatings

| Group | Formula viscosity (mPa · S) | Air flow rate (cfh) | Nozzle | Droplet Size | Spray Rate | Spray Distance | Visual Examination | Sq P (nm) | Wq (nm) | Rq (nm) |
|---|---|---|---|---|---|---|---|---|---|---|
| A | 6-16 | 8-12 | 0.2 mm, <0.5 mm needle retraction | <100 μm | <0.6 ml/min, | ~5 cm | Uniform white coating. No visible defects | 799.2 ± 227.8 | 216.7 ± 51.7 | 671.9 ± 167.5 |
| C | 3-7 | 4-6 | 0.2 mm, >0.5 mm needle retraction | about 10% of particle size >100 μm | <0.6 ml/min, | ~5 cm | Coarse coating with visible dried droplets due to large particle size | 904.0 ± 194.9 | 376.8 ± 87.7 | 734.8 ± 177.7 |

(iii) Negative Impact of Faster Spray Rates May be Mitigated by Increasing Spray Distance In order to determine if spray rates above 0.6 milliliters per minute may be used to obtain a uniform coating by more than 10 milliliters per minute are unlikely to be effective in a uniform coating preparation since the spray distance may need to be increased beyond 20 centimeters, which may not be practical for precisely spraying teeth in an oral cavity.

TABLE 4

Impact of faster spray rate in combination with increased spray distance.

| Group | Formula viscosity (mPa · S) | Air flow rate (cfh) | Nozzle | Droplet Size | Spray Rate | Spray Distance | Visual Examination | Sq P (nm) | Wq (nm) | Rq (nm) |
|---|---|---|---|---|---|---|---|---|---|---|
| D | 2-4 | 10-12 | 0.3 mm, >0.5 mm needle retraction | <100 μm | ~9.0 ml/min | Spray distance ~20 cm, | Uniform white coating without visible defects | 805.1 ± 85.9 | 213.1 ± 36.5 | 741.5 ± 80.9 |
| E | 2-4 | 12-16 | 0.3 mm, >0.5 mm needle retraction | <100 μm | ~10.3 ml/min | Spray distance ~20 cm, | Uneven coating with visible defects due to over-wetting | 1142.7 ± 86.1 | 421.7 ± 102.5 | 1013.9 ± 136.8 |

Example 2. In Vitro and In-Vivo Spray Coating on Tooth Surfaces

In order to assess whether the droplet size parameters and the spray rate parameters, discussed above, could be efficaciously used in a method to form a uniform coating on teeth, coating material was sprayed onto a bovine tooth block and on human teeth. The coating material, which was prepared as described in Table 1, was gently shaken before spraying onto 1) stained bovine tooth blocks 2) extracted human teeth and 3) the front teeth of ten panelists. Coating droplets were sprayed onto the foregoing tooth substrates using a 0.2 mm spray nozzle with needle retraction less than 0.5 mm at a flow rate of 12 cubic feet per hour. The spraying distance was about 5 cm. The volume-averaged droplet size was less than 100 μm and the droplets were delivered to the substrates at a rate of less than 0.6 milliliters per minute. The tooth surfaces were sprayed until the stains were no longer visible. The tooth surfaces were allowed to dry for up to three minutes, after which time a coating was formed.

Figure 2:
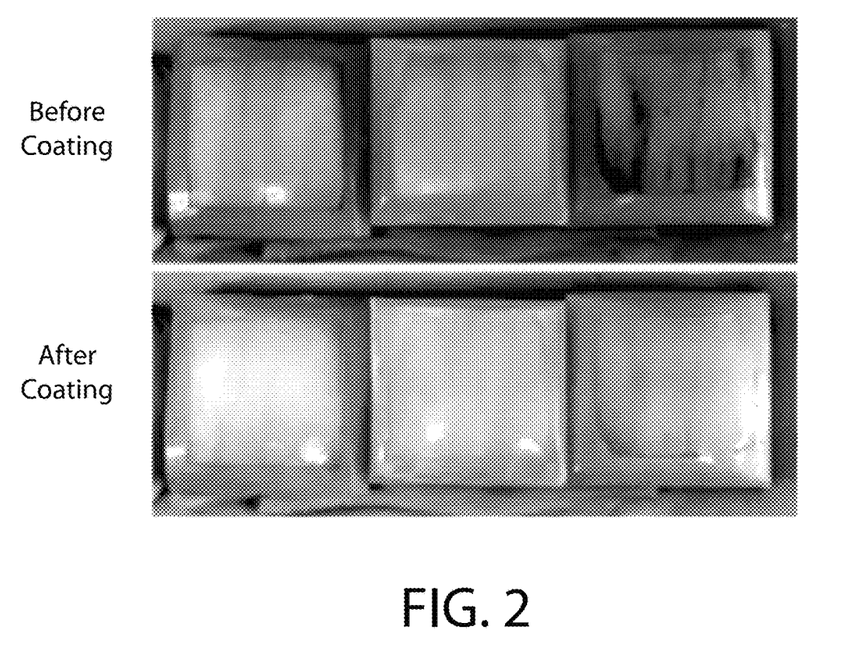
FIG. 2 shows examples of bovine tooth blocks before and after spraying with a whitening coating material as described in the Examples.

The results of spray coating bovine tooth blocks as described above are depicted in FIG. 2. The results are compared with the bovine tooth blocks before spraying. As is evident in FIG. 2, the bovine tooth blocks after spraying appear to be uniformly white with no visible defects. Further, the uniformly coated teeth match the whitest tooth on the VITA classical A1-D4 shade guide, Vita GmbH & Co. KG Bad Sackingen, Germany, demonstrating the efficacy of the instant method.

Figure 3:
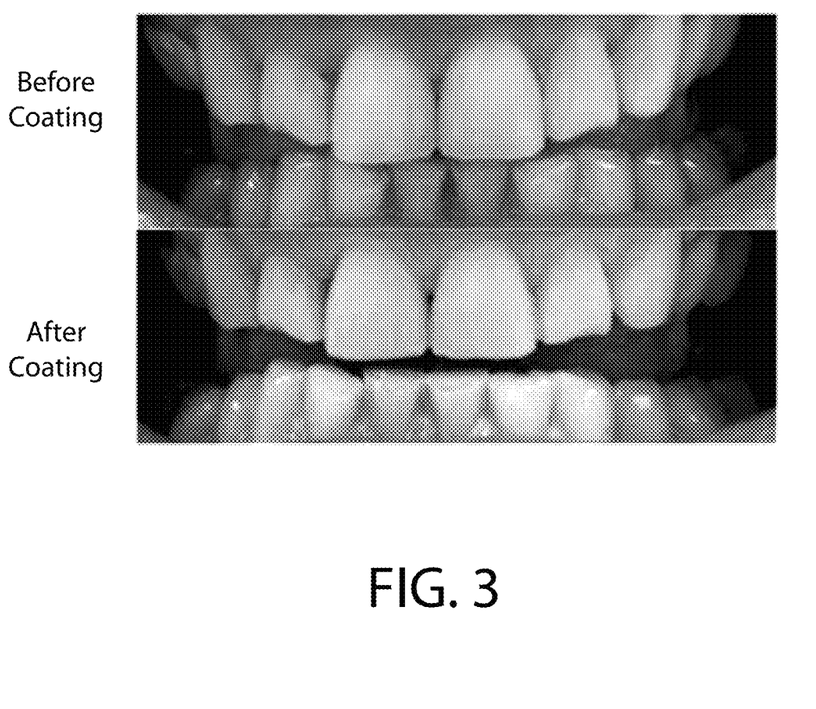
FIG. 3 shows examples of teeth from a human subject before and after spraying with a whitening coating material as described in the Examples.

The results of spray coating human teeth from one of the 10 panelists are depicted in FIG. 3. As is evident from FIG. 3, the human teeth after spraying, unlike the human teeth before spraying, appear to be uniformly white with no visible defects. Moreover, the uniformly coated tooth matches the whitest tooth on the VITA classical A1-D4 shade guide, further demonstrating the efficacy of the instant method.

What is claimed is:

1. A method of forming a uniform coating onto a tooth surface, which comprises:
    forming droplets by spraying an orally acceptable coating material through a spray nozzle; and
    depositing the droplets onto a tooth surface to form a uniform coating;
    wherein the droplets have a volume-averaged droplet size of less than 100 μm;
    wherein a spray comprising the droplets travels from a tip of the spray nozzle towards the tooth surface at a spray rate of about 9 milliliters/minute,
    wherein a spray distance is about 20 centimeters;
    wherein the atomization process comprises passing a stream of air through the spray nozzle;
    wherein the spray nozzle has a diameter of about 0.3 to about 0.5 millimeters;
    wherein a flow rate of the stream of air passing through the spray nozzle is from about 10 cubic feet per hour to about 12 cubic feet per hour;
    wherein the droplets comprise at least one substance selected from the group consisting of a film-forming polymer, a therapeutic agent and a cosmetic agent, and depositing the droplets onto the tooth surface to thereby form the uniform coating; and
    wherein the cosmetic agent is a whitening agent comprising whitening particles ranging in size from about 0.1 μm to about 10 μm, wherein the whitening particles have a refractive index greater than about 1.2.

2. The method of claim 1, wherein the droplets comprise an orally acceptable solvent and wherein the method further comprises evaporating the orally acceptable solvent on the tooth surface to thereby form the uniform coating.

3. The method of claim 2, wherein the orally acceptable solvent is ethanol.

4. The method of claim 1, wherein the spraying further comprises an atomization process selected from the group consisting of fluid pressure atomization, centrifugal force atomization, electrostatic charge atomization, ultrasonic atomization and gas pressure atomization.

5. The method of claim 4, wherein the gas pressure atomization is air pressure atomization.

6. The method of claim 1, wherein the spraying is performed with an airbrush.

7. The method of claim 1, wherein the uniform coating is visibly free of a coating defect selected from the group consisting of pinholes and dried droplets.

8. The method of claim 1, wherein the uniform coating is a film.

9. The method of claim 1, wherein the uniform coating is a dental sealant.

10. The method of claim 1, wherein the therapeutic agent is selected from the group consisting of a fluoride ion source, a calcium source, a stannous ion source, a zinc ion source, a potassium ion source, an antibacterial agent and combinations thereof.

11. The method of claim 1, wherein the whitening particles are selected from the group consisting of titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles and combinations thereof.

12. A method of forming a uniform coating onto a tooth surface comprising:
   providing a spray nozzle fluidly coupled to a reservoir, the reservoir containing an orally acceptable coating material that is in liquid form and the spray nozzle having a diameter ranging from about 0.2 mm to about 0.5 mm;
   performing an atomization step by applying a stream of air through the spray nozzle to convert at least some of the orally acceptable coating material from liquid form into droplets that exit a tip of the spray nozzle toward the tooth surface at a rate of less than about 0.6 milliliters/minute;
   depositing the droplets onto the tooth surface to form a uniform coating;
   wherein the droplets have a volume-averaged droplet size of less than 100 µm;
   wherein a flow rate of the stream of air passing through the spray nozzle is from about 8 cubic feet per hour to about 12 cubic feet per hour;
   wherein a spray distance is about 5 centimeters; and
   wherein the orally acceptable coating material comprises a film-forming polymer and whitening particles, the whitening particles ranging in size from about 0.1 µm to about 10 µm and have a refractive index greater than about 1.2, and wherein the droplets have a volume-averaged droplet size of about 100 µm.

* * * * *